United States Patent
Jimenez et al.

(10) Patent No.: US 12,073,333 B2
(45) Date of Patent: Aug. 27, 2024

(54) PREDICTING RATES OF HYPOGLYCEMIA BY A MACHINE LEARNING SYSTEM

(71) Applicant: Sanofi, Paris (FR)

(72) Inventors: Francisco Javier Jimenez Jimenez, Brookline, MA (US); Hsiaohui Wu, Ringoes, NJ (US); Fang Liz Zhou, Warren, NJ (US)

(73) Assignee: Sanofi, Paris (FR)

( * ) Notice: Subject to any disclaimer, the term of this patent is extended or adjusted under 35 U.S.C. 154(b) by 853 days.

(21) Appl. No.: 17/251,091

(22) PCT Filed: Jun. 21, 2019

(86) PCT No.: PCT/US2019/038454
§ 371 (c)(1),
(2) Date: Dec. 10, 2020

(87) PCT Pub. No.: WO2019/246511
PCT Pub. Date: Dec. 26, 2019

(65) Prior Publication Data
US 2021/0216894 A1    Jul. 15, 2021

Related U.S. Application Data (60) Provisional application No. 62/689,005, filed on Jun. 22, 2018.

(30) Foreign Application Priority Data

May 13, 2019 (EP) .................................... 19305609

(51) Int. Cl.
*G06N 5/04* (2023.01)
*G06N 20/00* (2019.01)
(Continued)

(52) U.S. Cl.
CPC ............... *G06N 5/04* (2013.01); *G06N 20/00* (2019.01); *G16H 10/60* (2018.01); *G16H 15/00* (2018.01); *G16H 50/20* (2018.01)

(58) Field of Classification Search
CPC .......... G06N 5/04; G06N 20/00; G16H 10/60; G16H 15/00; G16H 50/20
See application file for complete search history.

(56) References Cited

U.S. PATENT DOCUMENTS

| | | | | |
|---|---|---|---|---|
| 2011/0098220 A1* | 4/2011 | Wahren | ...................... | A61P 3/10 514/6.5 |
| 2017/0329917 A1* | 11/2017 | McRaith | ................ | G16H 20/00 |
| 2018/0150757 A1* | 5/2018 | Aggarwal | .............. | G06N 20/00 |

FOREIGN PATENT DOCUMENTS

| CN | 102770761 A | 11/2012 |
|---|---|---|
| CN | 106415556 A | 2/2017 |

(Continued)

OTHER PUBLICATIONS

American Diabetes Association, "Improving Care and Promoting Health in Populations: Standards of Medical Care in Diabetes—2018", Diabetes Care, 2018, 41(Suppl 1): S7-S12.

(Continued)

*Primary Examiner* — Pei Yong Weng
(74) *Attorney, Agent, or Firm* — Fish & Richardson P.C.

(57) ABSTRACT

Systems, methods, and computer products can predict rates of hypoglycemia in patients. One of the methods includes receiving data representing medical records of a patient, the patient having been diagnosed with diabetes mellitus. The method includes determine an predicted rate of hypoglycemic events using a machine learning system, the machine being trained using data representing the medical records of a plurality of patients and the corresponding rate of hypo- (Continued)

glycemic events for the respective patients. The methods also includes producing the predicted rate for the patient.

8 Claims, 5 Drawing Sheets

(51) Int. Cl.
　　G16H 10/60　　(2018.01)
　　G16H 15/00　　(2018.01)
　　G16H 50/20　　(2018.01)

(56) References Cited

FOREIGN PATENT DOCUMENTS

| | | |
|---|---|---|
| CN | 111833985 A | 10/2020 |
| JP | 2008-229330 A | 10/2008 |
| JP | 2013-503712 | 2/2013 |
| JP | 2013-543778 A | 12/2013 |
| WO | WO 2007/149533 | 12/2007 |
| WO | WO 2011/028925 | 3/2011 |
| WO | WO 2015/156965 A1 | 10/2015 |
| WO | WO 2019/246511 | 12/2019 |

OTHER PUBLICATIONS

Becker et al., "New insulin glargine 300 Units . mL-1 provides a more even activity profile and prolonged glycemic control at steady state compared with insulin glargine 100 Units . mL-1", Diabetes Care, 2015. 38(4):637-643.
Blonde et al., "Real-World Evidence Demonstrates Comparable Clinical Outcomes of Switching From Insulin Glargine 100 U/ML (GLA-100) to Insulin Glargine 300 U/ML (GLA-300) vs Insulin Degludec (IDEG) in Patients With Type 2 Diabetes (T2D)", Diabetes Technology & Therapeutics, 2018, 20(S1):A137-A138.
Bosnyak et al., ""Predictive Modeling of Hypoglycemia Risk with Basal Insulin Use in Type 2 Diabetes: Use of Machine Learning in the Lightning Study"", Diabetes Therapy, Feb. 2019, 11 pages.
Breiman, "Random forests", Machine Learning, 2001, 45(1):5-32.
Cabitza et al., "Unintended Consequences of Machine Learning in Medicine", JAMA, 2017, 318(6):517-518.
Centers for Disease Control and Prevention, "National Diabetes Statistics Report: Estimates of Diabetes and Its Burden in the United States, 2014", U.S. Department of Health and Human Services, 2014, 12 pages.
Cryer, "The barrier of hypoglycemia in diabetes", Diabetes, 2008, 57(12):3169-3176.
Cryer, "Hypoglycaemia: The limiting factor in the glycaemic management of type I and type II diabetes", Diabetologia, Jul. 2002, 45:937-948.
Cryer, "Hypoglycemia: still the limiting factor in the glycemic management of diabetes", Endocrine Practice, May 2008, 14(6):750-756.
DiCiccio et al., "Bootstrap confidence intervals", Statistical Science, 1996, 11(3):189-228.
Efron, "Estimation and Accuracy after Model Selection", Journal of the American Statistical Association, 2014, 109(507):991-1007.
Efron, "Nonparametric estimates of standard error: the jacknife, the bootstrap and other methods", Biometrika, Dec. 1981, 68(3):589-599.
Efron, "Model selection, estimation, and bootstrap smoothing", Stanford University, Aug. 2012, Technical Report 262, 26 pages.
Elliott et al., "Hypoglycemia Event Rates: A Comparison Between Real-World Data and Randomized Controlled Trial Populations in Insulin-Treated Diabetes", Diabetes Therapy, Mar. 2016, 7(1):45-60.
Dixon, "Bootstrap Resampling", Encyclopedia of Environmetrics, 2006, 9 pages.
Embrechts et al., "Hierarchical clustering for large data sets", Advances in Intelligent Signal Processing and Data Mining, Jan. 2013, pp. 197-233.
Evans et al., "Health-related quality of life associated with daytime and nocturnal hypoglycaemic events: a time trade-off survey in five countries", Health Qual Life Outcomes, 2013, 11:90, 9 pages.
Fabunmi et al., "Patient characteristics, drug adherence patterns, and hypoglycemia costs for patients with type 2 diabetes mellitus newly initiated on exenatide or insulin glargine", Current Medical Research and Opinion, Mar. 2009, 25(3):777-786.
Frier, "Hypoglycaemia in diabetes mellitus: epidemiology and clinical implications", Nat Rev Endocrinol, 2014. 10(12):711-722.
Ginde et al., "Validation of ICD-9-CM coding algorithm for improved identification of hypoglycemia visits", BMC endocrine Disorders, Apr. 2008, 8(4), 7 pages.
Gu et al., "Comparison of multivariate matching methods: structures, distances, and algorithms", Journal of Computational and Graphical Statistics, 1993, 2(4):405-420.
Guelman, "Gradient boosting trees for auto insurance loss cost modeling and prediction", Expert Systems with Applications, 2012, 39(3):3659-3667.
Heise et al., "Impact of the mode of protraction of basal insulin therapies on their pharmacokinetic and pharmacodynamic properties and resulting clinical outcomes", Diabetes, Obesity and Metabolism, 2017, 9(1):3-12.
Heise et al., "Insulin degludec: four times lower pharmacodynamic variability than insulin glargine under steady-state conditions in type 1 diabetes", Diabetes, Obesity and Metabolism, 2012. 14(9):859-864.
Heise et al., "Ultra-long-acting insulin degludec has a flat and stable glucose-lowering effect in type 2 diabetes" Diabetes, Obesity and Metabolism, 2012, 14(10):944-950.
UK Prospective Diabetes Study (UKPDS) Group, "Intensive blood-glucose control with sulphonylureas or insulin compared with conventional treatment and risk of complications in patients with Type 2 diabetes (UKPDS 33)", The Lancet, Sep. 1998, 352(9131):837-853.
International Hypoglycaemia Study Group, "Glucose concentrations of less than 3.0 mmol/L (54 mg/dL) should be reported in clinical trials: a joint position statement of the American Diabetes Association and the European Association for the study of diabetes", Diabetes Care, Jan. 2017, 40(1):155-157.
Khunti et al. ""Rates and predictors of hypoglycaemia in 27 585 people from 24 countries with insulin-treated type 1 and type 2 diabetes: the global HAT study"", Diabetes, Obesity and Metabolism, 2016, 18(9):907-915.
Klompas et al., "Automated detection and classification of type 1 versus type 2 diabetes using electronic health record data", Diabetes Care, Apr. 2013, 36(4):914-921.
Kosiborod et al., "Lower Risk of Heart Failure and Death in Patients Initiated on Sodium-Glucose Cotransporter-2 Inhibitors Versus Other Glucose-Lowering Drugs: The CVD-REAL Study (Comparative Effectiveness of Cardiovascular Outcomes in New Users of Sodium-Glucose Cotransporter-2 Inhibitors)", Circulation, 2017, 136(3):249-259.
Kuenen et al., "Does Glucose Variability Influence the Relationship Between Mean Plasma Glucose and HbA1c Levels in Type 1 and Type 2 Diabetic Patients?", Diabetes Care, Aug. 2011, 34(8):1843-1847.
Larranaga et al., "Machine learning in bioinformatics", Briefings in Bioinformatics, 2006, 7(1):86-112.
Lazzeroni et al., "P-values in genomics: Apparent precision masks high uncertainty", Molecular Psychiatry, Jan. 2014, 19(12):1336-1340.
Matsuhisa et al., "New insulin glargine 300 U/ml versus glargine 100 U/ml in Japanese adults with type 1 diabetes using basal and mealtime insulin: glucose control and hypoglycaemia in a randomized controlled trial (Edition JP 1)", Diabetes, Obesity and Metabolism, 2016, 18(4):375-383.
McEwan et al., "Healthcare resource implications of hypoglycemia-related hospital admissions and inpatient hypoglycemia: retrospective record-linked cohort studies in England", BMJ Open Diabetes Research and Care, Mar. 2015, 3(1):e00005.

(56) References Cited

OTHER PUBLICATIONS

Meneghini et al., "Association of hypoglycaemia severity with clinical, patient-reported and economic outcomes in US patients with type 2 diabetes using basal insulin", Diabetes, Obesity and Metabolism, 2018. 20(5):1156-1165.
Nelder et al., "Generalized Linear Models", Journal of the Royal Statistical Society. Series A (General), 1972, 135(3):370-384.
Nunes et al., "Assessing occurrence of hypoglycemia and its severity from electronic health records of patients with type 2 diabetes mellitus", Diabetes Research and Clinical Practice, Nov. 2016, 121:192-203.
Pathak et al., "Severe Hypoglycemia Requiring Medical Intervention in a Large Cohort of Adults With Diabetes Receiving Care in U.S. Integrated Health Care Delivery Systems: 2005-2011", Diabetes Care, 2016, 39(3):363-370.
PCT International Preliminary Report on Patentability in International Application No. PCT/US2019/038454, dated Dec. 22, 2020, 7 pages.
PCT International Search Report and Written Opinion in International Application No. PCT/US2019/038454, dated Sep. 23, 2019, 9 pages.
Pettus et al., "Rates of Hypoglycemia Predicted in Patients with Type 2 Diabetes on Insulin Glargine 300 U/ml Versus First and Second-Generation Basal Insulin Analogs: The Real-World Lightning Study", Diabetes Therapy, Feb. 2019, 17 pages.
Polonsky et al., "Poor medication adherence in type 2 diabetes: recognizing the scope of the problem and its key contributors", Patient Prefer Adherence, 2016. 10: 1299-1307.
Quilliam et al., "The incidence and costs of hypoglycemia in type 2 diabetes", The American Journal of Managed Care, Oct. 2011, 17(10):673-680.
Raju et al. "Hypoglycemia Incidence Rates and Associated Health Care Costs in Patients with Type 2 Diabetes Mellitus Treated with Second-Line Linagliptin or Sulfonylurea After Metformin Monotherapy", Journal of Managed Care & Specialty Pharmacy, May 2016, 22(5):483-492.
Ratner et al., "Hypoglycaemia risk with insulin degludec compared with insulin glargine in type 2 and type 1 diabetes: a pre-planned meta-analysis of phase 3 trials", Diabetes, Obesity and Metabolism, 2013, 15(2):175-184.
Ritzel et al., "A Randomized Controlled Trial Comparing Efficacy and Safety of Insulin Glargine 300 Units/mL Versus 100 Units/mL in Older People With Type 2 Diabetes: Results From the Senior Study", Diabetes Care, Aug. 2018, 41(8):1672-1680.
Ritzel et al., "Patient-level meta-analysis of the Edition 1, 2 and 3 studies: glycaemic control and hypoglycaemia with new insulin glargine 300 U/ml versus glargine 100 U/ml in people with type 2 diabetes", Diabetes, Obesity and Metabolism, 2015, 17(9):859-867.
Rosenstock et al., "More Similarities Than Differences Testing Insulin Glargine 300 Units/mL Versus Insulin Degludec 100 Units/mL in Insulin-Naive Type 2 Diabetes: The Randomized Head-to-Head Bright Trial", Diabetes Care, 2018, 41(10):2147-2154.
Rowley et al., "Diabetes 2030: Insights from Yesterday, Today, and Future Trends", Population Health Management, Feb. 2017, 20(1):6-12.
Rys et al., "Systematic review and meta-analysis of randomized clinical trials comparing efficacy and safety outcomes of insulin glargine with NPH insulin, premixed insulin preparations or with insulin detemir in type 2 diabetes mellitus", Acta diabetologica, Jan. 2015, 52(4):649-662.
news.sanofi.us [online], "In Senior Adults Treated with Basal Insulin, Switching to Sanofi's Toujeo® Halved Hypoglycemia Risk", Jun. 10, 2017, retrieved on Feb. 9, 2021, retrieved from URL < http://www.news.sanofi.us/2017-06-10-In-Senior-Adults-Treated-with-Basal-Insulin-Switching-to-Sanofis-Toujeo-R-Halved-Hypoglycemia-Risk>, 4 pages.
Sharma et al., "Trends in incidence, prevalence and prescribing in type 2 diabetes mellitus between 2000 and 2013 in primary care: a retrospective cohort study", BMJ Open, 6:e010210, 12 pages.
Sherman et al., "Real-World Evidence—What Is It and What Can It Tell Us?", The New England Journal of Medicine, 2016, 375(23):2293-2297.
Sterling et al., "Development of a simple noninvasive index to predict significant fibrosis in patients with HIV/HCV coinfection", Hepatology, 2006, 43:1317-1325.
Sullivan et al., "Clinical outcomes in real-world patients with type 2 diabetes switching from first- to second-generation basal insulin analogues: Comparative effectiveness of insulin glargine 300 units/mL and insulin degludec in the Deliver D+ cohort study", Diabetes, Obesity and Metabolism, 2018, 20(9):2148-58.
Terauchi et al., "New insulin glargine 300 U/ml versus glargine 100 U/ml in Japanese people with type 2 diabetes using basal insulin and oral antihyperglycaemic drugs: glucose control and hypoglycaemia in a randomized controlled trial (Edition JP 2)", Diabetes, Obesity and Metabolism, 2016, 18(4):366-374.
The Diabetes Control and Complications Trial Research Group, "The effect of intensive treatment of diabetes on the development and progression of long-term complications in insulin-dependent diabetes mellitus", The New England Journal of Medicine, Sep. 1993, 329(14):977-986.
Tibshirani, "Regression shrinkage and selection via the Lasso", Journal of the Royal Statistical Society. Series B (methodological), 1996. 58 (1): 267-288.
Wager et al., "Estimation and Inference of Heterogeneous Treatment Effects using Random Forests", Journal of the American Statistical Association, 2017, 29 pages.
Wysham et al., "Effect of Insulin Degludec vs Insulin Glargine U100 on Hypoglycemia in Patients With Type 2 Diabetes: The Switch 2 Randomized Clinical Trial", JAMA, 2017, 318(1):45-56.
Ye et al., "Prediction of Incident Hypertension Within the Next Year: Prospective Study Using Statewide Electronic Health Records and Machine Learning", Journal of Medical Internet Research, 2018, 20(1):e22.
Zhou et al., "Real-world evidence on clinical and economic outcomes of switching to insulin glargine 300 Units/mL vs other basal insulins in patients with type 2 diabetes on basal insulin", Diabetes Obesity and Metabolism, 2017, 20(5):1293-1297.

* cited by examiner

PREDICTING RATES OF HYPOGLYCEMIA BY A MACHINE LEARNING SYSTEM

CLAIM OF PRIORITY

This application is a 371 U.S. National Stage Application of PCT/US2019/038454, filed on, Jun. 21, 2019 which claims the benefit of European Application No. 19305609.0, filed on May 13, 2019 and U.S. Provisional Patent Application Ser. No. 62/689,005, filed Jun. 22, 2018, the entire contents of which are hereby incorporated by reference.

BACKGROUND

Machine learning is a subset of artificial intelligence in the field of computer science that often uses statistical techniques to give computers the ability to "learn" (i.e., progressively improve performance on a specific task) with data, without being explicitly programmed.

SUMMARY

In general, one innovative aspect of the subject matter described in this specification can be embodied in methods that include the act of receiving data representing medical records of a patient, the patient having been diagnosed with diabetes mellitus. The methods include the act of determining a predicted rate of hypoglycemic events using a machine learning system, the machine being trained using data representing the medical records of a plurality of patients and the corresponding rate of hypoglycemic events for the respective patients. The method also includes the act of producing the predicted rate for the patient.

The preceding and other embodiments can each optionally include one or more of the following features, alone or in combination. Each of the plurality of patients may use the same type of basal insulin. The methods may include the acts of determining a second predicted rate of hypoglycemic events using a second machine learning system, the second machine being trained using data representing the medical records of a second plurality of patients and the corresponding rate of hypoglycemic events for the respective second patients, wherein each of the second plurality of patients using the second type of basal insulin, the second type of basal insulin being different from the first type of basal insulin, and comparing the first predicted rate to the second predicted rate. The methods may include the act of recommending a basal insulin for the patient based on the comparing. The methods may include the acts of determining a plurality of predicted rates of hypoglycemic events for a second plurality of patients by providing data corresponding to the medical records of each of the second plurality of patients to the machine learning system, identifying one or more covariates in the data that correlates to an predicted rate of hypoglycemic events based on the data and the plurality of predicted rates of hypoglycemic events, and producing a report that identifies the one or more covariates and the corresponding predicted rate of hypoglycemic events. The methods may include the acts of determining a plurality of predicted rates of hypoglycemic events for a second plurality of patients by providing data corresponding to the medical records of each of the second plurality of patients to the machine learning system, each of the second plurality of patients having the same covariate and producing a report that identifies the covariate and the corresponding predicted rate of hypoglycemic events.

The present disclosure also provides a computer-readable storage medium coupled to one or more processors and having instructions stored thereon which, when executed by the one or more processors, cause the one or more processors to perform operations by implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations by implementations of the methods provided herein.

It is appreciated that implementations by the present disclosure can include any combination of the aspects and features described herein. That is, implementations by the present disclosure are not limited to the combinations of aspects, and features specifically described herein, but also include any other appropriate combinations of the aspects and features provided.

The details of one or more embodiments of the subject matter described in this specification are outlined in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Diabetes mellitus is the 7th leading cause of mortality and is a major cause of morbidity in the United States (US). It affects an estimated 29.1 million of the US population, with 1.4 million new diagnoses each year. The number of affect patients is expected to increase to more than 54.9 million by 2030. In 2012, total costs of diagnosed diabetes in the US was $245 billion ($176 billion for direct medical costs and $69 billion for reduced productivity).

Given the significant and growing burden of disease, complications associated with diabetes are becoming increasingly important to prevent and manage effectively. Hypoglycemia is a frequent and potentially fatal adverse effect of insulins and oral antidiabetic drugs (OADs) in diabetic patients. In addition to the immediate risk hypoglycemia poses, recurrent episodes result in fear of future episodes and have been shown to constitute both a patient-led and physician-led barrier to optimal glycemic control. The resultant increase in hemoglobin A1c (HbA1c) levels have been linked to an increased risk of microvascular (and potentially macrovascular) complications.

It is estimated that type 1 diabetics (T1DM) experience on average two mild hypoglycemic events per week and one severe event per year. However, event rates from randomized clinical trials for type 1 patients, expressed as per patient per year, ranges from 0.15 for severe events to 88.3 for non-severe events. Event rates for type 2 diabetics (T2DM) are considerably more variable between studies and range from 0.05 to 26.6 events per patient per year for severe and non-severe events respectively. However, studies have suggested that these studies grossly underestimate the true event rate of hypoglycemia in the real world, particularly for severe events.

The average cost of hypoglycemic events is also heterogeneous between studies, and difficult to pool due to differences in definitions of hypoglycemia and cost estimation methodologies. Current estimates of the average cost of an inpatient hypoglycemic event range from $2,205 to $17,564. Average outpatient costs per hypoglycemic event range from $148 to $501.

Different basal insulins have shown differential rates of hypoglycemia. For example, multiple studies demonstrated the superiority of insulin glargine 100 units/ml (Lantus) compared to protamine insulin in relation to severe hypoglycemic events. Some basal insulin, such as insulin glargine 300 units/ml (Toujeo), demonstrates a flatter, more prolonged pharmacokinetic and pharmacodynamic profile relative to others, with sustained blood glucose control beyond 24 hours.

The burden of hypoglycemia in the US is therefore substantial, and significant gains can be had by identifying the appropriate type of basal insulin for each patient. Estimation of the cost savings for the payor from the resultant reduced medical costs for these patients may help guide payor formulary decisions and drug pricing negotiations.

Figure 1:
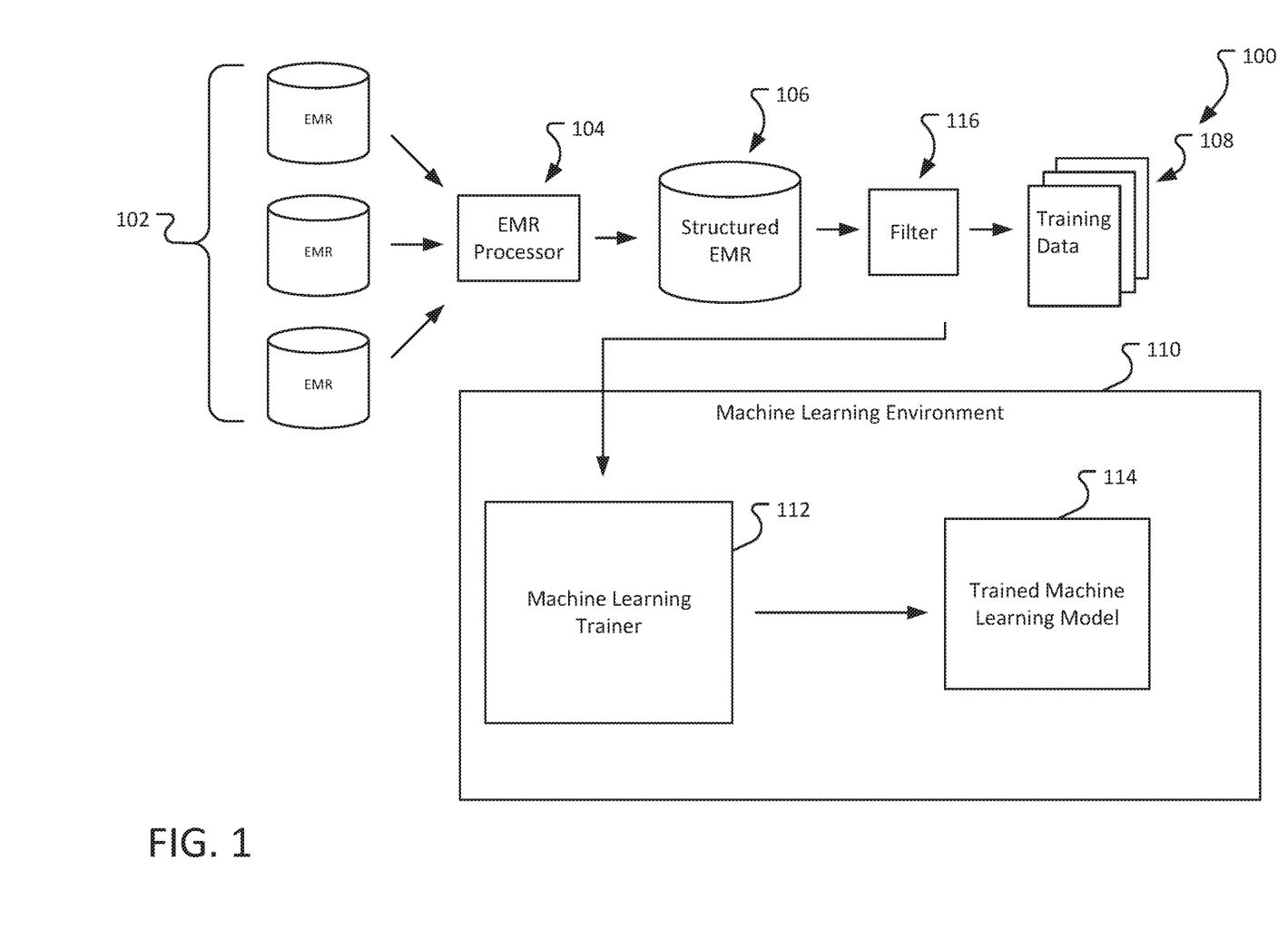
FIG. 1 illustrates an environment in which machine-learning models are trained to predict an expected rate for hypoglycemic events.

FIG. 1 illustrates an environment 100 in which machine learning models can be trained to predict an expected rate for hypoglycemic events. The system described herein uses electronic medical record data (EMR) 102 (which may be obtained from multiple different sources, including but not limited to hospital records and physician records) to train a machine learning system. In some implementations, the EMR may include information on demographic and socioeconomic categories, coded diagnoses and procedures, prescribed and administered medications, laboratory results, and clinical administrative data. In some implementations, the EMR may be processed by a processor 104. For example, EMR may include both structured and unstructured data. Structured data may include information such as the date of the visit, the patients name, etc. Unstructured data may include freeform text added by the physician (such as doctor's notes, a visit summary, etc.). The EMR processor may use techniques such as natural language processing to extract facts from the unstructured data in the EMR and turn it into structured EMR data 106.

In some implementations, the EMR processor 104 may filter some of the medical records. For example, the EMR processor 104 may only select medical records for patients that share values a particular variable (referred to as a covariate). Examples of covariates can include, for example, gender, geographic region, rate, age range, insurance carrier, years since diagnosis, HbA1c range, body mass index, blood pressure range, diabetic complications, alcohol and/or drug use, and any other physiological or demographic characteristic. The EMR processor 104 may be, for example, one or more computer systems as described below.

In some implementations, the same manually-created covariates can be used for the descriptive analyses, predictive modeling for hypoglycaemic rate, and analysis for cost estimation. The predetermined covariates may be based on expert clinical review of literature around hypoglycaemic event and cost predictors. Predetermined covariates can be defined using ICD-9 and ICD-10 diagnosis codes, laboratory values, and drug names and/or National Drug Code (NDC) codes. The EHR dataset (and not insurance claims) can be used to identify the covariates, unless the covariate is cost-related, in which case insurance claims data can be used.

A default look-back period may be one year prior to treatment start can be used, but it can also vary depending on how enduring the covariate is hypothesized to be. For example, the look-back period for cancer may be five years because if a patient has a diagnosis of cancer more than five years ago and no diagnoses subsequently, they are unlikely to have active cancer at the index date. For covariates where the extent of history does not influence their likelihood of capture in the dataset, e.g., gender and race, the look-back period can be eight years or may be limited only by the amount of available data. For irreversible and chronic conditions, the maximum look-back period may also be eight years or may be limited only by the amount of available data.

An example of categories of covariates used for both the hypoglycemic rate model and cost estimation analysis and their look-back period may be:

1. Demographics
   a. The look-back period for these covariates is eight years
2. Socioeconomics
   b. The look-back period for these covariates is eight years
3. Comorbidities
   c. The look-back period for these covariates range from 1 year (for reversible/acute conditions) to 8 years (for irreversible/chronic conditions)
   d. The Charlson Comorbidity Index (CCI) score as a distinct covariate within the comorbidity category. The CCI represents a measure of a patient's comorbid conditions (including diabetic complication category), associated with the pre-index period, including diabetic complications.
4. Diabetic complications
   e. The look-back period for these covariates is eight years
5. Diabetes disease status
   a. The look-back period for these covariates is one year for prior hypoglycemic events and eight years for the known duration of diabetes in the dataset
6. Medication use
   a. The look-back period for these covariates is one year Additional covariates may be included as part of a cost estimation analysis only (and not the hypoglycemic rate prediction) as these are expected to be drivers of hypoglycemia-related cost (and not hypoglycemic rate):

1. Physician specialty:
   f. The look-back period is all available data for "physician specialty" covariate, and two years for "physician's most commonly prescribed insulin."
2. Prior average hypoglycemic event cost
   g. The look-back period for this covariate is one year A further set of covariates can be determined. This set of covariates may not be pre-specified, but encompass all comorbidities, procedures, and prescriptions (collectively referred to as a 'markers' in the following) present in 1 year prior to the patients' index date can be included in the predictive modeling.

In some implementations, the following approach for unsupervised covariate creation may be used
1. The distance between markers is defined:
   a. Each marker is associated with a vector containing the set of patients for which the marker is true or false
   b. The distance between the markers then is the Jaccard distance between the vectors
2. Clusters based on these distances were then produced:
   a. Hierarchical clustering based on the distance matrix was performed, resulting in a cluster hierarchy. The average distance between clusters was used for hierarchically linking clusters
3. The level of hierarchy for extracting clusters is defined:
   a. The "inconsistency" method was used to determine at which level of the hierarchy we want to extract clusters. "Inconsistency" refers to the inconsistency of the average distances in the clusters being linked: Large values suggest clusters should not be linked
4. Clusters that many patient-treatments "exhibit" can be selected:
   a. Of the 1,500 clusters formed, the 100 exhibited by most patient-treatments was selected
   b. A patient-treatment was said to "exhibit" a cluster if during the one year before index date they had any of the diagnoses, procedures, or prescriptions (e.g., markers) that comprised the cluster
5. Medical rationalization of clusters:
   a. Clinical experts subsequently checked the derived clusters for medical logic, validating the parameters used for the unsupervised cluster generation.

In some implementations, the EMR records may be filtered prior to generating training data 108 but after generating the structure medical record 106, for example, by a filter 116.

The structured EMR data 106 may be used to generate training records 108 (collectively a training set). The training records may be representative of the available data in the structured EMR data. For example, in some implementations, a portion of the structured EMR records may be used to train a machine learning system while the remaining records are used to validate the trained machine learning system. In some implementations, training records can be created at the level of a "patient-treatment" during which a patient was on basal insulin treatment. Accordingly, multiple training records can be created for an individual patient. The unit of analysis is "patient-treatment", defined as the period in which a patient is observed on a basal insulin treatment in the dataset (the period between a treatment index and a treatment observation end). Hypoglycemic events are the target endpoints only within this patient-treatment period.

Treatment index date can be defined as the date of either of the following: very first start of prescription of any basal insulin; or change of prescription from one basal insulin to another. The basal insulins in baseline included: Gla-300, Gla-100, IDet, IDeg and NPH. Index basal insulins of interest for the study were: Gla-300, Gla-100, IDet, and IDeg.

For purposes of rate calculation, the "duration" can be taken to be the duration of the patient-treatment period as previously described minus the duration of all inpatient stays during this period.

In some implementations, the index date is the date of the first prescription of BI or the change of prescription from one basal insulin to another. Treatment end can be defined as either the end of the follow-up period in the dataset, the change of prescription from the index basal insulin to another BI or one year after treatment index date (whichever occurred earliest).

In one implementation, patient-treatments may be excluded from the training data if patient-treatment meets any of the following criteria:
1. Treatments with multiple types of basal insulin: that is, patient-treatments that start within one week of another treatment start (either before or after) for the same patient.
2. Patient-treatments with any period of inactivity longer than 270 days in the 365 days prior to index date (inactivity is defined as the lack of any time-stamped data in the relevant tables in the dataset).
3 Patient-treatments with treatment duration of less than one day.

Separately, inpatient stay is excluded from the duration of patient-treatment as patients are often switched to standard basal insulins on admission as per hospital provider formulary. As such, hypoglycemic events during inpatient stays cannot be attributed to the index basal insulin.

The training record may include information about hypoglycemic events. In some implementations, hypoglycemic events can be counted within the patient-treatment period. The duration for determining hypoglycemia rates was taken to be the duration of the patient-treatment period minus that of all inpatient stays during this period. The hypoglycemic events can be the expected output of the training set. For example, the training set can train a machine learning system to determine a likelihood of an expected number of hypoglycemic events within a fixed period (for example, a month, six months, one year, 5 years, etc.) Alternatively, the training set can train the machine learning system to determine an expected number of hypoglycemic events within a time period (for example, a month, six months, a year, 5 years, etc.)

Figure 2:
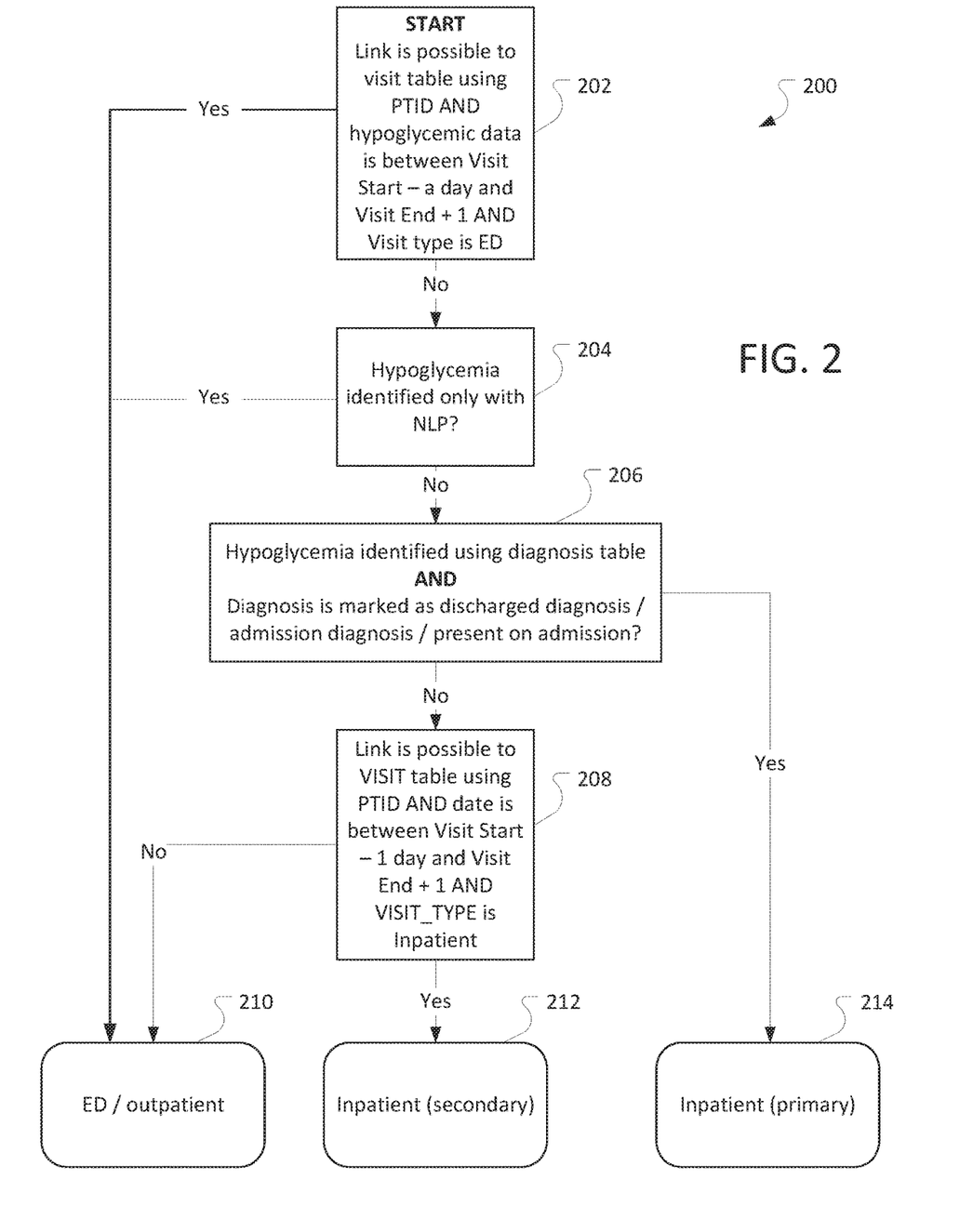
FIG. 2 is a flowchart illustrating an example of a process for categorizing an event as ED/outpatient, Inpatient (secondary), or Inpatient (primary).

Hypoglycemic event rates can include both severe and non-severe events. FIG. 2 is a flow chart of an example of a process to categorize a hypoglycemic event as severe or non-severe. The definition of 'severe' hypoglycemia is may include, for example, ICD-9/10 codes that are severe by nature, administration of intramuscular glucagon. Further, natural language processing of the EMR maybe used to identify hypoglycemia. In terms of severity, any hypoglycemic events that were not severe can be defined as 'non-severe'.

In some implementations, an event is defined as hypoglycemia if any of the following criteria were met:
1. ICD-9 and 10 hypoglycemia diagnosis codes
2. Laboratory plasma glucose levels≤70 mg/dl
3. Administration of intramuscular glucagon
4 NLP output In some implementations, the NLP-recognized hypoglycemic events are defined as any mention of hypoglycemia excluding those with negative sentiment or indication of historic occurrence. For example, a "mention" of hypoglycemia may be any occurrence in term of the regular expression ".*hypoglyce.*", unless the term is exactly 1 of "hypoglycemic awareness", "hypoglycemic unawareness", or "neonatal hypoglycemia". A "negative sentiment" may be any indication that the reference to hypoglycemia was negative, indicating for instance that it did not occur. Historic occurrence is a record that indicates that the reference is to an event in the past (e.g. "patient has history of hypoglycemia"). In some implementations, a list of negative sentiment and historic keywords can used to exclude accompanying hypoglycemia mentions.

In some implementations, a maximum of one hypoglycemic event may be counted per calendar day. For example, if a hypoglycemic event is recorded by multiple sites of care, or by multiple definition criteria, only one event is counted.

In some implementations, a hypoglycemic event can be defined as severe if any of the following conditions are met:
1. The hypoglycemia ICD-9 or 10 diagnosis code is severe by default (ICD-9 249.30: 250.30; 250.31: 251.0; ICD-10 E08.641; E09.641; E10.641; E11.641; E13.641; E15)
2. The ICD code for hypoglycemia is flagged as the admitting diagnosis, primary reason for care on discharge, or present on admission
3. The hypoglycemia start date occurs on same day as an Emergency Department (ED) visit or inpatient admission
4. There is a plasma glucose measurement <54 mg/dl
5. Intramuscular glucagon was administered
6. The NLP mention of hypoglycemia is accompanied by a descriptor of severity—including severity terms (e.g. "severe") and attributes (e.g. "emergency")
7. The NLP hypoglycemic event occurs on the same day as an ED visit or inpatient admission A machine-learning environment 110 can include a machine learning trainer 112. The machine learning trainer 112 can train a machine learning model 114 to predict an expect rate of hypoglycemic events for different patients. The trained machine learning system may be used in a variety of different ways, including identifying the most appropriate basal insulin for patient related to the hypoglycemic outcome for patients, thereby improving the health of the patient.

Generally, machine learning can encompass a wide variety of different techniques that are used to train a machine to perform specific tasks without being specifically programmed to perform those tasks. The machine can be trained using different machine learning techniques, including, for example, supervised learning, unsupervised learning, and reinforcement learning. In supervised learning, inputs and corresponding outputs of interest are provided to the machine. The machine adjusts its functions in order to provide the desired output when the inputs are provided. Supervised learning is generally used to teach a computer to solve problems in which are outcome determinative, for example, the training set 108 may be used to train the trained machine learning model 114 to predict a likelihood of a hypoglycemic event for a given patient or group of patients. In contrast, in unsupervised learning inputs are provided without providing a corresponding desired output. Unsupervised learning is generally used in classification problems such as, customer segmentation (for example, segmenting patients into different groups based on characteristics associated with hypoglycemic events). Reinforcement learning describes an algorithm which a machine makes decisions using trial and error. Feedback informs the machine when a good choice or bad choice is made. The machine then adjusts its algorithms accordingly.

During the training process, different algorithms may be used, including among others, generalized linear regression (GLM). Poisson GLM is an algorithm used to model discrete counts based on independent inputs.

In order to develop a trained machine learning system that is capable of accurately predicting a rate of hypoglycemic events, the machine learning model 114 may be to be trained with information that is not misleading. However, patient treatment of diabetes (and other medical conditions) can be fluid. For example, patients may switch from one type of basal insulin to another. Accordingly, in some implementations, EMR 102 of some patients (and therefore corresponding training data 108) may be excluded from the training data.

FIG. 2 is a flow chart illustrating an example of a process for categorizing an event as ED/outpatient (outcome 210), Inpatient (secondary) (outcome 212), or Inpatient (primary) (outcome 214).

An event may be defined as being primary inpatient (outcome 214) if it meets all the following criteria:
1. If the event can be linked to the visit table and the visit type is not ED (Step 202)
2. The hypoglycemic events are not only identified by natural language processing. (Step 304)
3. The event can be found using the diagnosis table (Step 206)
4. The diagnosis is marked as "discharge diagnosis", "admission diagnosis", or "present on admission"

An event may be defined as secondary inpatient if it meets all the following criteria:
1. The hypoglycemic events are not only identified by NLP (Step 204)
2. If the event can be found using the diagnosis table, the diagnosis is not marked as "discharge diagnosis", "admission diagnosis", or "present on admission" (Step 206)
3. The event can be linked to the visit table using PTID, the visit type is inpatient, and the hypoglycemic event date is between visit start date minus 1 day and visit end date plus 1 day (this is to allow a buffer for linking hypoglycemic events to visits given there is often not an exact date match in dataset) (Step 208)

In some implementations, as described above secondary inpatient events may be excluded as patients are often switched to a different basal insulin and their dosage altered for the duration of their inpatient stay. As such, any hypoglycemic events during this period cannot be attributed to the patient's usual insulin.

For example, an event can be defined as outpatient/ED (outcome 210) if it meets any of the following:
1. The event can be linked to the visit table using PTID, the visit type is ED, and the hypoglycemic event date is between visit start date minus 1 day and visit end date plus 1 day (Step 202)
2. The event is identified using only natural language processing (Step 204)
3. The event is not identified using only NLP, if it can be identified using the diagnosis table, the diagnosis is not marked as discharge diagnosis, admitting diagnosis, or present on admission, and no link can be made to the visit table (Step 206)

Once the training records are created, they can be used to train a machine learning system. Different types of machine learning models can be trained.

For example, the trained learning model may be embodied as a generalized linear model. Different types of generalized linear models may be appropriate in various scenarios. A zero-inflated negative binomial GLM (zNBGLM) was used because it models a discrete count of events occurring in a given time period, by estimating the per-patient hypoglycemic event rates most likely to have resulted in the hypoglycemic counts seen in the data. One downside of a zNBGLM is that the model allows for very many degrees of freedom and tended to over-fit the data for smaller segments, thus degrading generalization performance. Another type of generalized linear model is a Poisson GLM. A Poisson GLM is well suited to modeling discrete counts but does not allow for 'over-dispersion' (i.e. it constrains the variance to be equal to the mean). The Poisson GLM used the number of hypoglycemic events as the target variable (outcome) and the length of observation as an offset variable.

In another example, the trained learning model may be embodied as an artificial neural network. Artificial neural networks (ANNs) or connectionist systems are computing systems inspired by the biological neural networks that constitute animal brains. An ANN is based on a collection of connected units or nodes, called artificial. Each connection, like the synapses in a biological brain, can transmit a signal from one artificial neuron to another. An artificial neuron that receives a signal can process it and then signal additional artificial neurons connected to it.

In common ANN implementations, the signal at a connection between artificial neurons is a real number, and the output of each artificial neuron is computed by some non-linear function of the sum of its inputs. The connections between artificial neurons are called 'edges'. Artificial neurons and edges may have a weight that adjusts as learning proceeds (for example, each input to an artificial neuron may be separately weighted). The weight increases or decreases the strength of the signal at a connection. Artificial neurons may have a threshold such that the signal is only sent if the aggregate signal crosses that threshold. The transfer functions along the edges usually have a sigmoid shape, but they may also take the form of other non-linear functions, piecewise linear functions, or step functions. Typically, artificial neurons are aggregated into layers. Different layers may perform different kinds of transformations on their inputs. Signals travel from the first layer (the input layer), to the last layer (the output layer), possibly after traversing the layers multiple times.

In some implementations, the machine learning system may be used to identify hypoglycemic event rates and hypoglycemia costs. Least absolute shrinkage and selection operator (LASSO) regularization can be used to select variables. In order to verify the models, the models can developed ('trained') on 80% of each treatment-specific cohort (termed the 'training sets'). Ten-fold cross-validation may be used to inform model selection and model parameter optimization. Models may then be then validated on the remaining 20% of each treatment-specific cohort (internal validation). Bootstrapping can be used to evaluate the variability of model estimates (i.e. to generate confidence intervals).

Once the machine learning system is trained, the system can be used to identify patients who are likely to have lower number of hypoglycemic events if treated with one kind of basal insulin compared to another. For example, once a model is trained for each type of basal insulin and for the number of severe and non-severe hypoglycemic events. Each model can then be applied to the entire basal-insulin treated population to obtain insulin-specific hypoglycemia rate prediction (that is, an estimate of the hypoglycemia rate in the total population if all patients were using a specific basal insulin).

The system can then compare the hypoglycemic rate for patients based on different variables.

Figure 3:
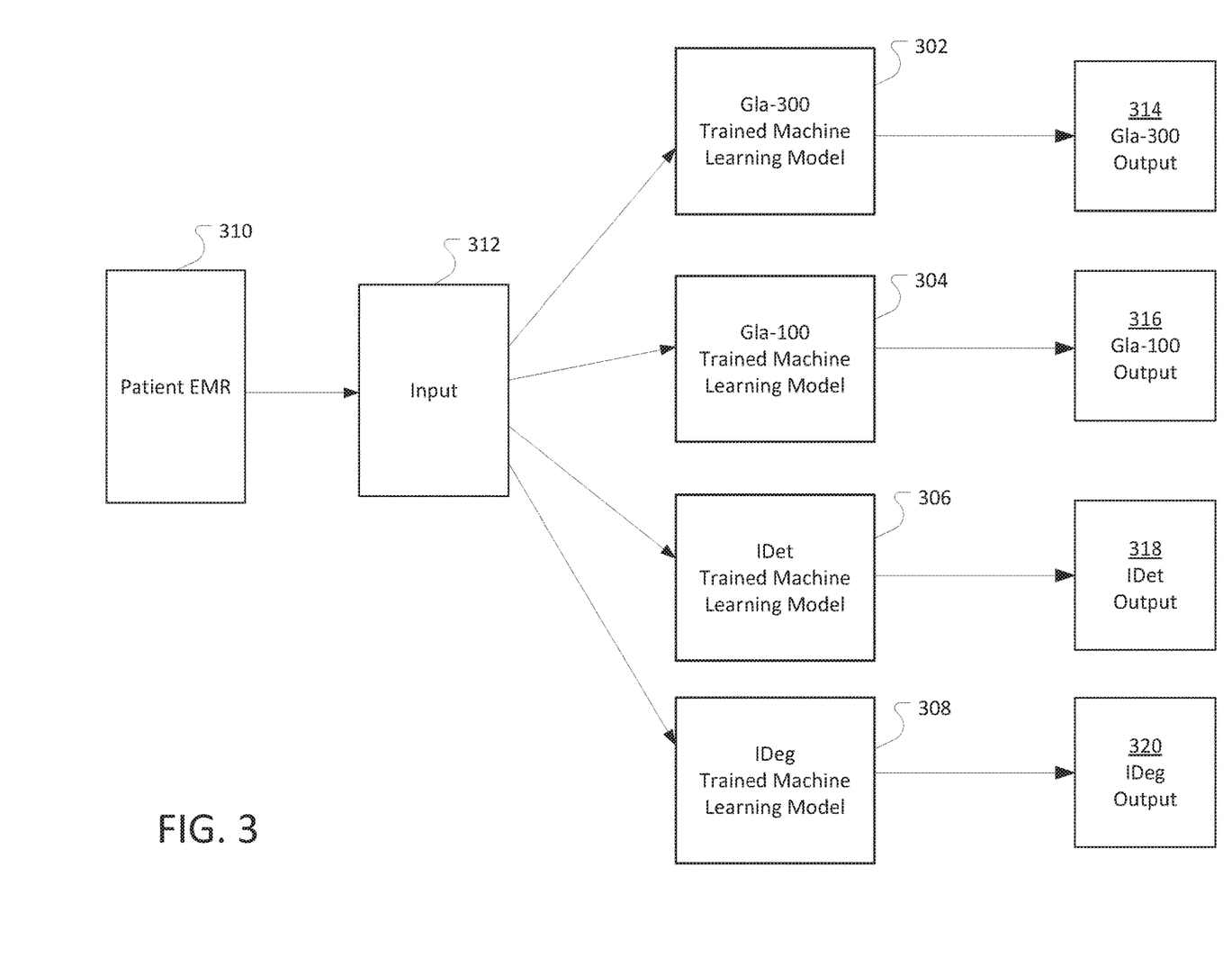
FIG. 3 illustrates an example process for determining hypoglycemic rates for various covariates.

FIG. 3 illustrates an example of using a trained machine learning models. Patient EMR 310 can be processed to generate an input 312. The input 312 can be provided to each of the trained machine learning models, in this example the Gla-300 trained machine learning model, the Gla-100 trained machine learning model 304, the IDet trained machine learning model 306, and the IDeg trained machine learning model 308. Each model may product an output. For example, the Gla-300 trained machine learning model 302 generates the Gla-300 output 314, the Gla-100 trained machine learning model 304 generates the Gla-100 output 316, the IDet trained machine learning model 306 generates the IDet output 318, and the IDeg trained machine learning model 308 generates the IDeg output 320.

In some implementations, as described above, two trained machine learning models may be generated for each type of basal insulin. The first trained machine learning model may be trained to determine an expected rate of severe hypoglycemic events. A second trained machine learning model may be trained to determine an expected rate of non-severe hypoglycemic events.

The results of processing these covariates using the machine learning system can be analyzed to identify correlations between different covariates and different hypoglycemic rates for different types of basal insulin. For example, linear regression models can be used to identify correlations between the different co-variates and the outcomes predicted by the models.

In some implementations, covariates of interest may also be determined by the machine learning system. For example, learning machine may be trained to cluster individuals based on, for example, the rate and severity of hypoglycemic events across the multiple variables. In this manner, the machine learning system may identify covariates that may have otherwise gone unnoticed.

In some implementations, a cost model can be built to predict the cost of a hypoglycemic event in the T2DM population using the EMR and training dataset. In some implementations, the dataset used for the treatment cost modeling included all hypoglycemic events in EHRs for T2DM patients who were at least 18 years of age at the time of the event and who had linked claims data. Severe hypoglycemic events with a cost of $0 were excluded. Study period and covariates were the same as those described for the hypoglycemia prediction models except when covariates could not be created due to data limitation.

Gradient-boosted trees (using prediction errors from previous decision trees to improve performance of subsequent trees) can be utilized for cost estimation, which have been successful in cost prediction previously; they allowed the capture of non-linear, complex relationships underlying hypoglycemia cost. The cost estimator was applied to the subgroups identified as drivers of differential hypoglycemic rate, to estimate the cost per hypoglycemic event for each subgroup. When subgroups had key defining variables missing due to data limitation, an overall model cost estimate for a hypoglycemic event was used for the subgroups. Cost saving at subgroup level was calculated by applying the subgroup-specific cost estimate of a hypoglycemic event to the delta hypoglycemic event rate between comparator and reference BI.

Figure 4:
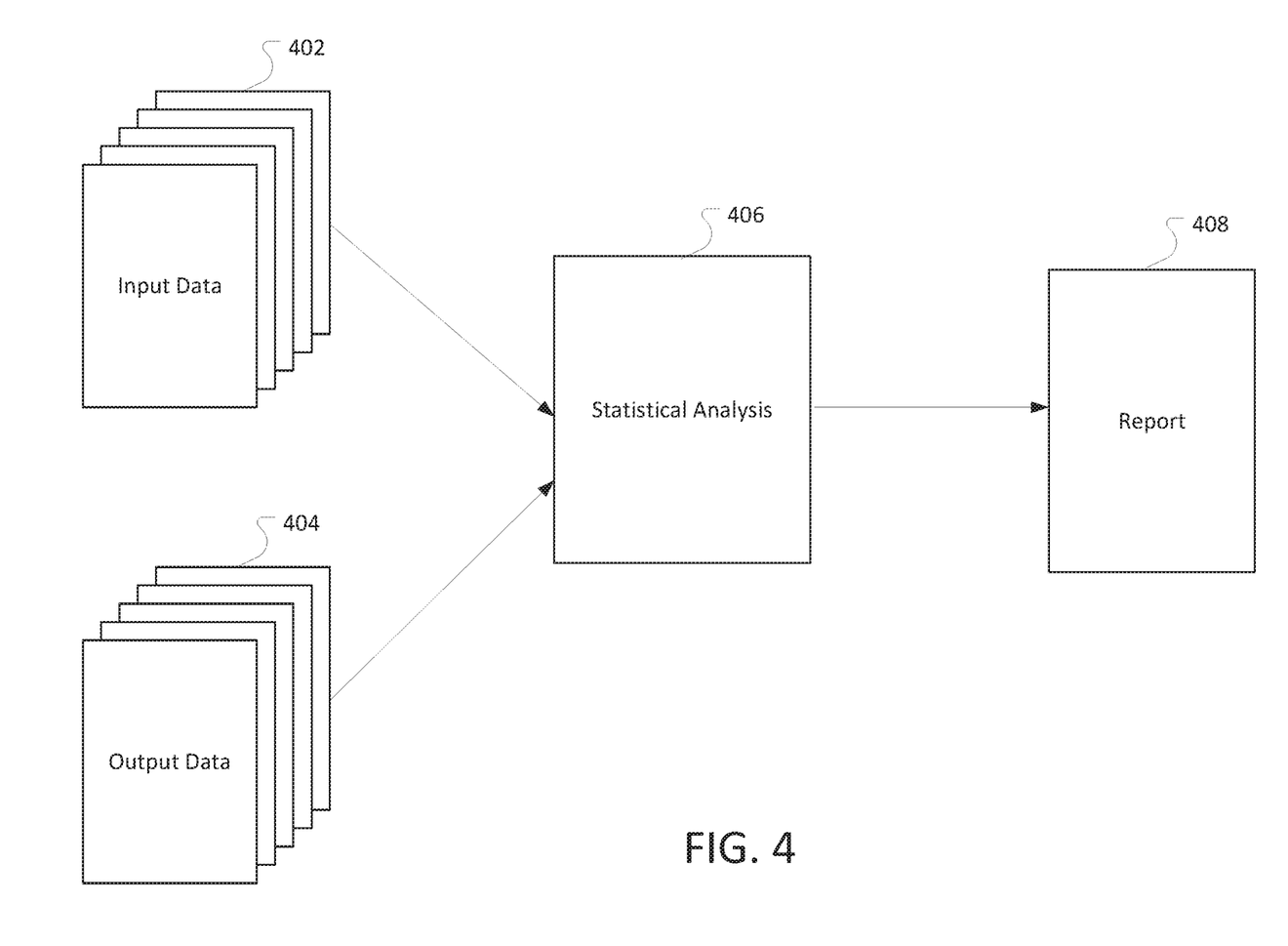
FIG. 4 illustrates an example of determining hypoglycemic rates for various covariates.

FIG. 4 illustrates an example of determining hypoglycemic rates for various covariates. Input Data 402 that is provided to a machine learning system and the corresponding output data 404 from a machine learning system as described above, may be provided to a statistical analysis system 406. The statistical analysis system may identify correlations and relationships between different variables in the output data using different statistical techniques. The correlations and relationships may be presented as a report 408.

Another use for the trained machine learning models includes identifying a type of basal insulin that is appropriate for a particular patient. For example, the trained machine learning system may take the patient's medical records and input.

The medical records can be provided to each of the trained machine learning models. As described above, each model has been used to predict the number of hypoglycemic incidents (or the probability that a hypoglycemic incident will occur) severe or non-severe.

The system can propose a basal insulin based on the results from the models. In some implementations, the system may propose the basal insulin with lower risk of a severe hypoglycemic event (or a non-severe hypoglycemic event.). In some implementations, the system may determine the cost saving of using a particular basal insulin regime compared to another associated with hypoglycemic events and propose the solution that reduces hypoglycemia related costs. In some implementations, the system may propose the basal insulin that reduces the rate of hypoglycemic event, but, if two different basal insulins produce results that are within a threshold value (for example, within 1%, 5%, or 10% efficacy) then the system may propose the less expensive basal insulin.

In another embodiment, the trained learning machine models may be used to identify patients that are more likely to have a hypoglycemic event. For example, the system may access a patient's medical records, identify the type of basal insulin that the patient is using, and process the medical records though a corresponding trained machine learning model. The trained machine learning model produces an indication of the likelihood or expected frequency and/or severity of a hypoglycemic event. If the indication exceeds a threshold value (for example, more than 1 event per week, or a 20% likelihood of a severe hypoglycemic event) then the patient and/or the patients physician may be notified.

Figure 5:
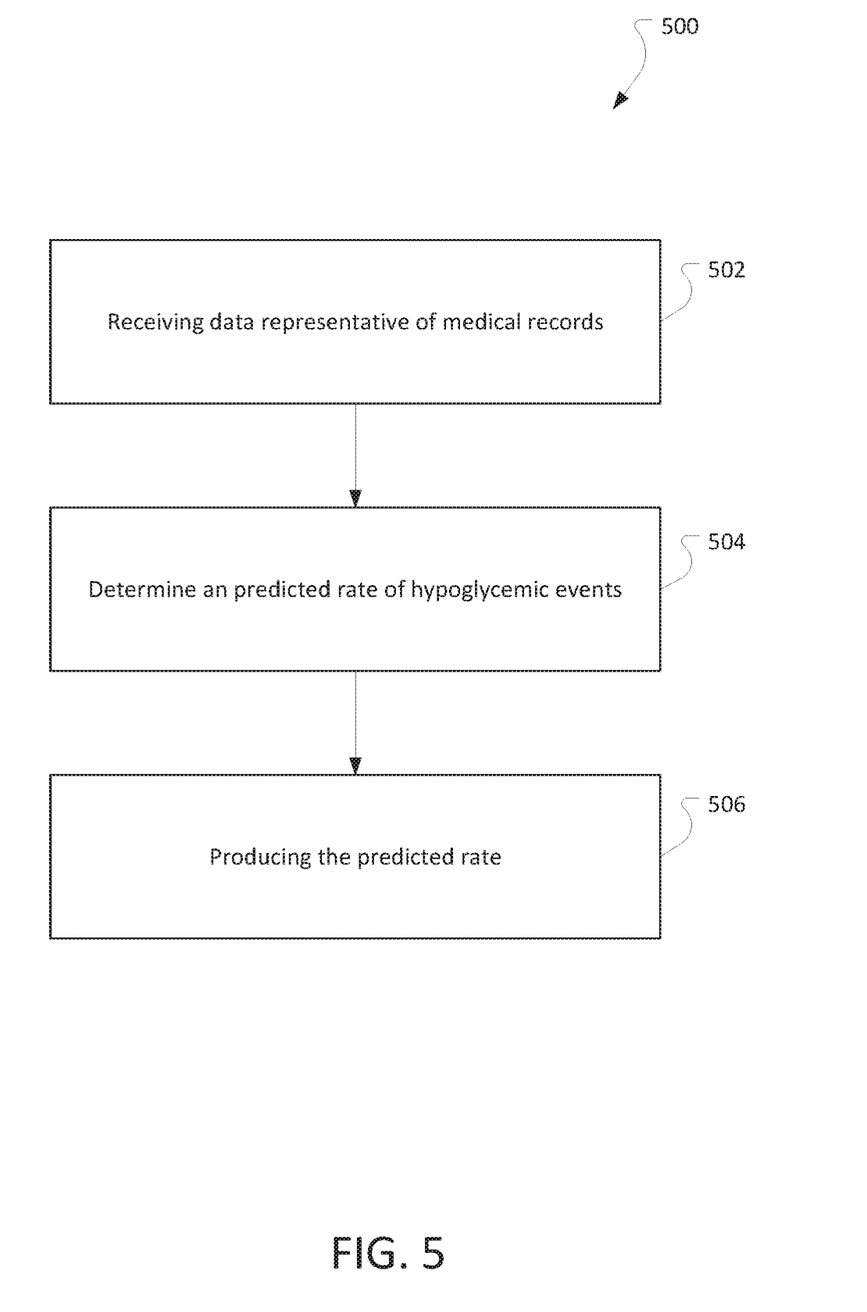
FIG. 5 is a flowchart of an example of a process for using patient data to generate a trained machine-learning model.

FIG. 5 is a flow chart of an example of a process 500 for using patient data to generate a trained machine learning model. The process 500 may be performed by one or more of the computer systems as described below.

The process 500 receives 502 data representing medical records of a patient, the patient having been diagnosed with diabetes mellitus.

The process 500 determines 504 an expected rate of hypoglycemic events using a machine learning system, the machine being trained using data representing the medical records of a plurality of patients and the corresponding rate of hypoglycemic events for the respective patients. In some implementations, teach of the plurality of patients uses the same type of basal insulin.

The process 500 produces 506 the expected rate for the patient.

In some implementations, the process 500 may include determining a second expected rate of hypoglycemic events using a second machine learning system, the second machine being trained using data representing the medical records of a second plurality of patients and the corresponding rate of hypoglycemic events for the respective second patients, wherein each of the second plurality of patients using the second type of basal insulin, the second type of basal insulin being different from the first type of basal insulin; and comparing the first expected rate to the second expected rate.

In some implementations, the process 500 may include recommending a basal insulin for the patient based on the comparing.

In some implementations, the process 500 may include determining a plurality of expected rates of hypoglycemic events for a second plurality of patients by providing data corresponding to the medical records of each of the second plurality of patients to the machine learning system, identifying one or more covariates in the data that correlates to an expected rate of hypoglycemic events based on the data and the plurality of expected rates of hypoglycemic events, and producing a report that identifies the one or more covariates and the corresponding expected rate of hypoglycemic events.

In some implementations, the process 500 may include determining a plurality of expected rates of hypoglycemic events for a second plurality of patients by providing data corresponding to the medical records of each of the second plurality of patients to the machine learning system, each of the second plurality of patients having the same covariate, and producing a report that identifies the covariate and the corresponding expected rate of hypoglycemic events.

Embodiments of the subject matter and the functional operations described in this specification can be implemented in digital electronic circuitry, tangibly-embodied computer software or firmware, computer hardware (including the structures disclosed in this specification and their structural equivalents), or in combinations of one or more of them. Embodiments of the subject matter described in this specification can be implemented as one or more computer programs (i.e., one or more modules of computer program instructions encoded on a tangible non-transitory program carrier for execution by, or to control the operation of, data processing apparatus). The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example, a programmable processor, a computer, or multiple processors or computers. The apparatus can also be or further include special purpose logic circuitry (e.g., an FPGA (field programmable gate array) or an ASIC (application-specific integrated circuit)). In addition to hardware, the apparatus can optionally include code that creates an execution environment for computer programs (e.g., code that constitutes processor firmware, a protocol stack, a database management system, an operating system, or a combination of one or more of them).

A computer program, which can also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document, in a single file dedicated to the program in question, or in multiple coordinated files (e.g., files that store one or more modules, sub-programs, or portions of code)). A computer program can be deployed so that the program is executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry (e.g., an FPGA (field programmable gate array) or an ASIC (application-specific integrated circuit)).

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data (e.g., magnetic, magneto-optical disks, or optical disks), however, a computer need not have such devices. Moreover, a computer can be embedded in another device (e.g., a mobile telephone, a personal digital assistant (PDA), a mobile audio or video player, a game console, a Global Positioning System (GPS) receiver, or a portable storage device (e.g., a universal serial bus (USB) flash drive), to name just a few).

Computer-readable media suitable for storing computer program instructions and data include all forms of nonvolatile memory on media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user, for example, by sending web pages to a web browser on a user's device in response to requests received from the web browser.

Embodiments of the subject matter described in this specification can be implemented in a computing system that includes a back-end component (e.g., as a data server), or that includes a middleware component (e.g., an application server), or that includes a front-end component (e.g., a client computer having a graphical user interface or a web browser through which a user can interact with an implementation of the subject matter described in this specification), or any combination of one or more such back-end, middleware, or front-end components. The components of the system can be interconnected by any form or medium of digital data communication (e.g., a communication network). Examples of communication networks include a local area network (LAN) and a wide area network (WAN) (e.g., the Internet).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a user device (e.g., for purposes of displaying data to and receiving user input from a user interacting with the user device), which acts as a client. Data generated at the user device (e.g., a result of the user interaction) can be received from the user device at the server.

While this specification contains many specific implementation details, these should not be construed as limitations on the scope of any invention or on the scope of what can be claimed, but rather as descriptions of features that can be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing can be advantageous.

What is claimed is:

1. A method implemented by a computer system, the method comprising:
   receiving data representing medical records of a patient, the patient having been diagnosed with diabetes mellitus;
   generating a model input using the data representing the medical records of the patient;
   determining a first predicted rate of hypoglycemic events by processing the model input using a first machine learning model that has been trained using first training data that comprises data representing medical records of a first plurality of patients and corresponding rates of hypoglycemic events for the respective patients, wherein each of the first plurality of patients uses a first type of insulin;
   determining a second predicted rate of hypoglycemic events by processing the model input using a second machine learning model that has been trained using second training data that comprises data representing medical records of a second plurality of patients and corresponding rates of hypoglycemic events for the respective patients, wherein each of the second plurality of patients uses a second type of insulin, the second type of insulin being different from the first type of insulin, and the second plurality of patients being different from the first plurality of patients;

comparing the first predicted rate to the second predicted rate; and recommending an insulin treatment for the patient based on the comparing.

2. The method of claim 1, further comprising:

determining a plurality of predicted rates of hypoglycemic events for a third plurality of patients by providing data corresponding to the medical records of each of the third plurality of patients to one of the machine learning models;

identifying one or more covariates in the data that correlate to a third predicted rate of hypoglycemic events based on the data and the plurality of predicted rates of hypoglycemic events; and producing a report that identifies the one or more covariates and the corresponding third predicted rate of hypoglycemic events.

3. The method of claim 1, further comprising:

determining a plurality of predicted rates of hypoglycemic events for a third plurality of patients by providing data corresponding to the medical records of each of the third plurality of patients to one of the machine learning models, each of the third plurality of patients having the same covariate; and producing a report that identifies the covariate and a third corresponding predicted rate of hypoglycemic events.

4. A non-transitory computer readable medium encoded with computer program instructions that when executed by one or more computers cause the one or more computers to perform operations comprising:

receiving data representing medical records of a patient, the patient having been diagnosed with diabetes mellitus;

generating a model input using the data representing the medical records of the patient;

determining a first predicted rate of hypoglycemic events by processing the model input using a first machine learning model that has been trained using first training data that comprises data representing medical records of a first plurality of patients and corresponding rates of hypoglycemic events for the respective patients, wherein each of the first plurality of patients uses a first type of insulin;

determining a second predicted rate of hypoglycemic events by processing the model input using a second machine learning model that has been trained using second training data that comprises data representing medical records of a second plurality of patients and corresponding rates of hypoglycemic events for the respective patients, wherein each of the second plurality of patients uses a second type of insulin, the second type of insulin being different from the first type of insulin, and the second plurality of patients being different from the first plurality of patients;

comparing the first predicted rate to the second predicted rate; and recommending an insulin treatment for the patient based on the comparing.

5. The non-transitory computer readable medium of claim 4, wherein the operations further comprise:

determining a plurality of predicted rates of hypoglycemic events for a third plurality of patients by providing data corresponding to the medical records of each of the third plurality of patients to one of the machine learning models;

identifying one or more covariates in the data that correlate to a third predicted rate of hypoglycemic events based on the data and the plurality of predicted rates of hypoglycemic events; and producing a report that identifies the one or more covariates and the corresponding third predicted rate of hypoglycemic events.

6. The non-transitory computer readable medium of claim 4, wherein the operations further comprise:

determining a plurality of predicted rates of hypoglycemic events for a third plurality of patients by providing data corresponding to the medical records of each of the third plurality of patients to one of the machine learning models, each of the second plurality of patients having the same covariate; and producing a report that identifies the covariate and a third corresponding predicted rate of hypoglycemic events.

7. A system comprising:

one or more computers and one or more storage devices storing instructions that are operable, when executed by the one or more computers, to cause the one or more computers to perform operations comprising:

receiving data representing medical records of a patient, the patient having been diagnosed with diabetes mellitus;

generating a model input using the data representing the medical records of the patient;

determining a first predicted rate of hypoglycemic events by processing the model input using a first machine learning model that has been trained using first training data that comprises data representing medical records of a first plurality of patients and corresponding rates of hypoglycemic events for the respective patients, wherein each of the first plurality of patients uses a first type of insulin;

determining a second predicted rate of hypoglycemic events by processing the model input using a second machine learning model that has been trained using second training data that comprises data representing medical records of a second plurality of patients and corresponding rates of hypoglycemic events for the respective patients, wherein each of the second plurality of patients uses a second type of insulin, the second type of insulin being different from the first type of insulin, and the second plurality of patients being different from the first plurality of patients;

comparing the first predicted rate to the second predicted rate; and recommending an insulin treatment for the patient based on the comparing.

8. The system of claim 7, wherein the operations further comprise:

determining a plurality of predicted rates of hypoglycemic events for a third plurality of patients by providing data corresponding to the medical records of each of the third plurality of patients to one of the machine learning models;

identifying one or more covariates in the data that correlate to a third predicted rate of hypoglycemic events based on the data and the plurality of predicted rates of hypoglycemic events; and producing a report that identifies the one or more covariates and the corresponding third predicted rate of hypoglycemic events.

\* \* \* \* \*